(12) United States Patent
Ahonen et al.

(10) Patent No.: US 8,838,225 B2
(45) Date of Patent: Sep. 16, 2014

(54) ANALYSIS OF MULTI-CHANNEL MEASUREMENT DATA USING ORTHOGONAL VIRTUAL CHANNELS

(75) Inventors: Antti Ahonen, Stockholm (SE); Matti Kajola, Stockholm (SE); Jukka Nenonen, Stockholm (SE); Juha Simola, Stockholm (SE); Samu Taulu, Stockholm (SE)

(73) Assignee: Elekta AB (publ), Stockholm (SE)

( * ) Notice: Subject to any disclaimer, the term of this patent is extended or adjusted under 35 U.S.C. 154(b) by 2018 days.

(21) Appl. No.: 11/654,029

(22) Filed: Jan. 17, 2007

(65) Prior Publication Data

US 2008/0161714 A1    Jul. 3, 2008

(30) Foreign Application Priority Data

Jan. 3, 2007    (JP) .................. 2007-000010

(51) Int. Cl.
*A61B 5/04*    (2006.01)
*A61B 5/0476*    (2006.01)
*A61B 5/0478*    (2006.01)

(52) U.S. Cl.
CPC ............. *A61B 5/0476* (2013.01); *A61B 5/0478* (2013.01)
USPC .......................................... 600/544; 600/545

(58) Field of Classification Search
USPC .................. 600/544–545; 702/127, 189–191; 324/244–245, 256–258; 327/510
See application file for complete search history.

(56) References Cited

U.S. PATENT DOCUMENTS 4,974,602 A * 12/1990 Abraham-Fuchs et al. .. 600/544
2006/0031038 A1 * 2/2006 Simola et al. ................. 702/127

FOREIGN PATENT DOCUMENTS

WO    WO-2006/114473    11/2006

OTHER PUBLICATIONS

S. Taulu et al., "Applications of the Signal Space Separation Method", IEEE Transactions on Signal Processing, Sep. 2005, pp. 3359-3372, vol. 53, No. 9.
C. Shannon, "Communication in the Presence of Noise", Proceedings of the IEEE, Feb. 1998, pp. 447-457, vol. 86, No. 2.
P.K. Kemppainen et al., "Channel Capacity of Multichannel Magnetometers", Low Temperature Laboratory, Helsinki University of Technology, pp. 635-638, Finland.
J. Nenonen et al., "Total Information of Multichannel MEG Sensor Arrays", Elekta Neuromag Oy.
M. Huang et al., Vector-based spatial-temporal minimum L1-norm solution for MEG, NeuroImage, pp. 1-13.
E. Pihko et al., "Somatosensory evoked potentials and magnetic fields elicited by tactile stimulation of the hand during active and quiet sleep in newborns,", Clinical Neurophysiology 115 (2004), pp. 448-455.

(Continued)

Primary Examiner — Michael D'Angelo
(74) Attorney, Agent, or Firm — Studebaker & Brackett PC

(57) ABSTRACT

The present invention introduces a method for processing multichannel measurement data achieved especially in MEG and EEG measurements. The method uses a signal space separation (SSS) method and the orthogonality of lead fields in order to calculate linear transformation from physical measurement channels to virtual channels. The geometry related to the measurement arrangement is dissipated and the number of virtual channels is clearly lower than the number of physical sensors. The concept of total information can be applied for such transformed measurement data due to orthogonality. The method offers simplified post-processing of the biomagnetic data, such as for source modelling. The total information can also be interpreted as a robust quantity describing the physiological state of a patient.

33 Claims, 3 Drawing Sheets

(56) References Cited

OTHER PUBLICATIONS

T. Imada et al., "Infant speech perception activates Brocas's area: a developmental magnetoencephalography study", Institute for Learning and Brain Sciences, pp. 957-962, vol. 17, No. 10, Jul. 17, 2006.

M. Cheour et al., "Magnetoencephalography is feasible for infant assessment of auditory discrimination", Experimental Neurology, pp. S44-S51, vol. 190, 2004.

K. Uutela et al., "Visualization of Magnetoencephalograhic Data Using Minimum Current Estimates", Brain Research Unit, Low Temperature laboratory, and Institute of Mathematics, Helsinki University of Technology pp. 173-180, Dec. 1, 1998.

S. Taulu et al., "Presentation of Electromagnetic Multichannel Data: The Signal Space Separations Method", Journal of Applied Physics, pp. 124905-124905-10, Helsinki, Finland.

S. Taulu et al., "Spatiotemporal Signal Space Separation Method for rejecting Nearby Interference in MEG Measurements", Physics in Medicine and Biology, pp. 1759-1768, Helsinki, Finland.

\* cited by examiner

ANALYSIS OF MULTI-CHANNEL MEASUREMENT DATA USING ORTHOGONAL VIRTUAL CHANNELS

BACKGROUND OF THE INVENTION

1. Field of the Invention

The invention relates to biomagnetic measurements and especially magnetoencephalographic (MEG) and electroencephalographic (EEG) measurements.

2. Description of the Related Art

It is possible to measure biomagnetic, that is, neural fields originating in brain tissue with magnetoencephalographic (MEG) measurement devices. Ionic currents which flow in the dendrites of neurons, induce a detectable magnetic field. There is a need for extremely sensitive detecting devices such as SQUIDs (Superconducting Quantum Interference Devices) because the biomagnetic signals are very small (in the order of femtoteslas) in amplitude in the MEG measurements. Therefore, those signals are very easily buried under external interference signals which typically have much higher amplitudes.

Other brain activity measurement techniques include electroencephalography (EEG), where the potential differences between different parts of the brain are measured. Electrodes are placed on the surface of the head, and the amplitude and the duration of the voltage differences between the electrodes are changing according to brain activity such as according to the state of consciousness.

Prior art publication US 2006031038 discloses a so-called SSS method (Signal Space Separation) where the measured biomagnetic signal can be divided into sums of signal components which originate in different volumes. This method can be used for eliminating interferences because the method separates biomagnetic signals from external interferences based merely on the basic physics of electromagnetic fields (that is, Maxwell's equations) and on the geometry used in the measurement.

Explaining the SSS method in a more thorough manner, a magnetic field measured by a multi-channel MEG device is analysed by examining three different volumes of the measurement geometry. The interesting source is in measurement volume V1 and the sensors are in measurement volume V2 outside volume V1. The sources of magnetic interferences and the compensation actuators are outside the aforementioned volumes in volume V3. In this examination, the V3 can also be infinite in volume. In the method, the magnetic field produced by the interesting sources disposed in volume V1 is parametrised in volume V2 as a sum of elementary fields, each of them being irrotational, sourceless and finite outside volume V1 so that a presentation of a desired accuracy is achieved for the parametrised magnetic field in volume V2. Similarly, the sum magnetic field produced by the interference fields and compensation actuators disposed in volume V3 is parameterised in volume V2 as a sum of elementary fields. The measuring device's signal vectors corresponding to each elementary field are calculated. If a magnetic signal is measured using sensors, then thereafter, the fields produced from sources disposed in different volumes can be separated by calculating the components of the measured signal vector in the basis formed by the signal vectors associated with the elementary fields.

As another application using MEG measurements, FI 20050445 discloses a method for interference suppression. In this case the source of interference is located e.g. in a patient's head or neck where it is close to the source of biomagnetic signals. In FI 20050445, two different series expansions are calculated from the measured signals. These two series expansions relate to the sources in the measurement area and to the sources outside that area. By identifying components which are present in both series expansions, the interference sources originating in the direct vicinity of the human brain, can be identified and suppressed.

The core problem in magnetoencephalography is a so-called inverse problem where the current source locations are to be estimated based on the measured magnetic fields outside the object. This is usually a rather tricky problem because in principle there is not a unique solution to the inverse problem. Solution of current source distributions can be attempted by using, e.g., minimum (Lp) norm estimates. The problem can also be constrained by using anatomical and physiological information.

A lead field of a given sensor in this context is a vector field in the source space to which the given sensor is most sensitive. Generally, in all non-parametric approaches to the source localization problem, the measured multichannel signal vector (signal values from different channels achieved by the physical sensors) is expressed as a product of a lead field matrix and a dipole moment vector, concatenated from 1-n current dipoles. The lead field matrix contains the lead fields of the physical sensors and the dipole moment vector corresponds to dipole moments to be estimated at selected points within the brain volume.

One prior art method for source localization in MEG measurements is described in Uutela et al.: "Visualization of magnetoencephalographic data using minimum current estimates", NeuroImage 10, 173-180, 1999 and Huang et al.: "Vector-based spatial-temporal minimum L1-norm solution for MEG", NeuroImage 31, 1025-37, 2006. It is a lead-field based solution where the minimum L1-norm solution selects the source configuration that minimizes the absolute value of the source strength and which can handle highly correlated sources.

Several other prior art methods are based on minimum L2-norm estimation which maximizes the smoothness of the solution. They also include beamformer approaches where source covariances estimated from the data are applied for focusing the solution at a selected point and at the same time reducing contributions from other source locations. In prior art publication 'Shannon: "Communication in the Presence of Noise", Proceedings of the IEEE, Vol. 86, No. 2, February 1998', a widely used Shannon's theory of communication has been presented. From there, a concept of total information can be derived. It has been used in theoretical calculations for capacities of multichannel SQUID arrays. Such channel capacity calculations have been performed e.g. in a publication 'Kemppainen, Ilmoniemi: "Channel capacity of multichannel magnetometers", Advances in Biomagnetism, Plenum Press, New York', where the total information per sample is obtained from:

$$I_{tot} = \frac{1}{2}\sum_{i=1}^{N} \log_2(SNR_i + 1) \quad (1)$$

where the SNR's are taken from orthogonalized channels (1, . . . , N).

Nenonen et al.: "Total Information of Multichannel MEG Sensor Arrays", Proc. Biomag 2004, pp. 630-631, discloses one way of calculating total information for multichannel sensor arrays used in MEG. Nenonen examines the optimal number of channels needed with a thin-film triple-sensor array placed around the patient's head on a helmet-shaped surface. Nenonen shows that the total information associated with the sensor array does not grow after a certain number of used channels. With triple-sensors the optimal value is approximately 320 channels while with magnetometers or axial gradiometers the optimal channel amount is approximately 250 channels.

In the prior art one problem is that though the quality of the measured data has been improved by suppressing interferences, the actual measurement data is still included in the same amount of measurement channels as before the signal processing. Therefore the handling of the data can be rather demanding computationally.

Another problem in prior art has been that the geometry associated with the measurement setup (the physical sensors, the apparatus and the measurable objects) has been maintained in the cases where some processing or transformation has been made to the MEG data.

Concerning the calculation complexity of prior art solutions, forward modeling of signals which correspond to the physical sensors require calculation of the magnetic flux through pick-up loops. This is accomplished by estimating the surface integral with a certain number of integration points for approximating the non-zero area of the loop. If the number of channels is N and the number of integration points is p, there are N*p calculations required for each current dipole. This often makes the lead field matrix calculation and the dipole fitting a computationally heavy procedure. Additionally because of the non-orthogonality or spatial overlapping of the lead fields, the lead field matrix is known to be ill-posed. As a consequence, e.g. minimum L1- and L2-norm solutions require numerical regularisation with suitable regularisation parameters. The correct selection of these parameters is generally difficult to be achieved. As a result, incorrect regularisation may lead to biased source reconstruction and false data analysis.

SUMMARY OF THE INVENTION

The present invention relates to a method for spatial processing of multi-channel measurement data, where multi-channel data is measured with plurality of sensors, and multipole moments are estimated from the measured data which multipole moments have orthogonal lead field expressions so that the measured data is represented in virtual channels while the geometry relating to the measurement setup is dissipated.

In one embodiment of the invention, the estimation step is performed with a signal space separation method, wherein a magnetic field that was registered using a multi-channel measuring device, is analysed in a geometry in which the sources of interest are disposed in volume V1; the sensors measuring the field or the components thereof in volume V2 outside volume V1; and sources of magnetic interference and compensating actuators (e.g. coils) in volume V3 outside both volumes V1 and V2, wherein volume V3 can be infinite. Furthermore, the magnetic field in volume V2 produced by the sources of interest is parametrised as a sum of elementary fields, each of them being irrotational, sourceless and finite outside volume V1 so that a presentation of a desired accuracy is achieved for the parametrised magnetic field in volume V2. Furthermore, the sum magnetic field in volume V2 produced by the interference sources and the compensating actuators in volume V3 is parametrised as a sum of elementary fields, each of them being irrotational, sourceless and finite outside volume V3 so that a presentation of a desired accuracy is achieved for the parametrised magnetic field in volume V2. Furthermore, the signal vector of the measuring device is calculated corresponding to each elementary field; the magnetic signal is measured using sensors; and the fields produced by sources disposed in different volumes are separated by estimating the components of the measured signal vector in the basis formed by the signal vectors associated with the elementary fields.

In one embodiment of the invention, the multipole moments are estimated with vector spherical harmonic functions.

In one embodiment of the invention, total information is extracted from the data represented in virtual channels.

In one embodiment of the invention, the number of virtual channels is adjusted to be less than the number of the plurality of sensors.

In one embodiment of the invention, the total information is calculated with a formula $$I_{tot} = \frac{1}{2}\sum_{i=1}^{N} \log_2(SNR_i + 1).$$

In one embodiment of the invention, the virtual channels represented by the multipole moments are set as point-like.

In one embodiment of the invention, the total information is used for estimating the physiological state of the patient, or for identifying and abandoning non-useful virtual channels or for optimizing the signal space separation decomposition results.

In one embodiment of the invention, external interferences are identified and processed with the signal space separation method and the external interferences are cancelled from the measurement data.

In one embodiment of the invention, movement of the measured target is identified and the effect of the movement of the measured target is cancelled with the signal space separation method.

In one embodiment of the invention, the method is applied in a magnetoencephalographic (MEG) measurement.

In one embodiment of the invention, the method is applied in an electroencephalographic (EEG) measurement.

Furthermore, the inventive idea also comprises a multi-channel measuring device for spatial processing of multi-channel measurement data. The device comprises a sensor array comprising plurality of sensors for measuring multi-channel data, and control means for controlling the measuring device, wherein the control means is configured to estimate from the measured data the multipole moments which have orthogonal lead field expressions so that the measured data is represented in virtual channels while the geometry relating to the measurement setup is dissipated.

The control means is configured to perform the method steps described above.

In one embodiment of the device, the control means is configured to identify and process external interferences with the signal space separation method, and the device comprises compensating actuators and the control means for cancelling the external interferences from the measurement data.

Furthermore, the inventive idea also comprises a computer program for spatial processing of multi-channel measurement data, comprising code adapted to perform the steps according to the previously described method, when the code is executed on a data-processing system.

The present invention has advantages over the prior art solutions. The main advantage is that the number of resulting channels is much less when the transformation method is applied to the MEG measurement data. The decrease in the amount of channels is however achieved with practically no loss of the actual information. There is also the advantage that the source reconstruction becomes less complex and more stable. A further advantage is that the movements of the patient's head and the geometry of the measurement are effectively embedded in the transformed virtual channel signals without the loss of important measurement data, thus resulting in simplified postprocessing of the virtual channel data. Furthermore, the method enables the virtual channels to be classified as relevant and irrelevant channels and therefore, the irrelevant virtual channels can be ignored without any loss of useful MEG data.

One further advantage is that existing and commonly known source reconstruction methods can be used after applying the algorithm. Because the idealized virtual channels can be thought of as point-like sensors, the algorithm needs only M calculations for each current dipole instead of the $N*p$ calculations of the physical channels (M is the number of the virtual channels). Therefore, the computational cost as a fraction is $M/(N*p)$. In one example for a typical apparatus, this fraction is $80/(306*8) \approx 3.3\%$. However, in practise, a single computation has a different cost for an idealised channel compared to a physical channel. Though, with the discussed implementation, the costs are estimated to be quite close to each other which renders the above calculation approximately correct.

Furthermore, the lead field gram matrix of the virtual channels is diagonal because of the orthogonality, and this means the matrix is numerically stable. Therefore, the user doesn't need to perform intervention for the numerical regularisation which further reduces analysis time and makes it less error-prone.

DETAILED DESCRIPTION OF THE EMBODIMENTS

Reference will now be made in detail to the embodiments of the present invention, examples of which are illustrated in the accompanying drawings.

The purpose of the present invention is to show an efficient way of idealizing the multi-channel MEG measurement data into device-independent form without any loss of relevant information. This is performed by transforming the measured MEG data into idealized virtual channels the number of which is smaller than the number of physical sensors.

Figure 1:
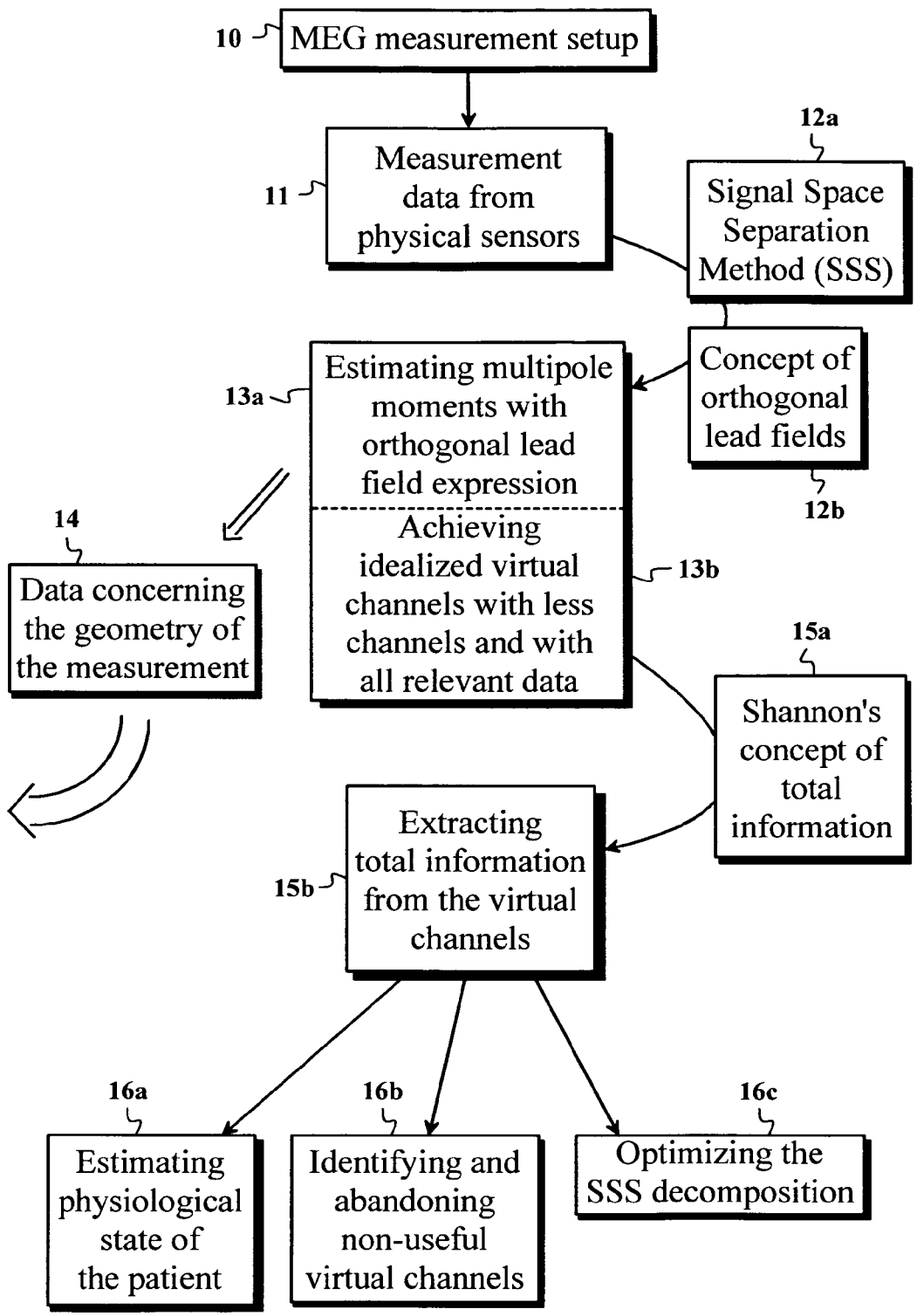
FIG. 1 is a block diagram illustrating one embodiment of the virtual channel calculation method according to the present invention.

FIG. 1 shows a flow diagram which represents the steps according to one embodiment of the invention. At first a setup 10 is created where the magnetoencephalography (MEG) apparatus is available for measuring biomagnetic signals from a patient. Typically these interesting biomagnetic signals originate in the patient's brain and their amplitude is very low compared to electromagnetic signals present in everyday environments. Thus, the setup of the MEG device includes very sensitive magnetometers such as e.g. SQUID sensors. Furthermore, it includes control electronics for receiving and processing the biomagnetic signals. It may include compensating actuators for creating magnetic fields which cancel the effect of external interference signals which normally would distort the measurement. Furthermore, the same effect may be created by placing the MEG apparatus inside a magnetically shielding room.

The MEG device typically has a large number of physical measurement channels represented by a group or array of sensors placed around the patient's head. Generally, in practise, the number of sensors (and thus, the number of physical channels) is typically a few hundred for reliable imaging of the brain signals. However, the present invention can be applied in any multi-channel measurement independent of the exact number of the used channels.

In phase 11 magnetic fields are measured by the array of physical sensors as a function of time. This measurement data is a starting point for further processing such as suppression of external interference. For one thing, there is a need for postprocessing of the measured signal because the inverse problem, which emerges during the source modelling procedure, may be highly unstable even with source constraints. Thus, some simplification to the measurement data has to be made in order to solve the inverse problem in an adequate manner.

The transformation of the measured data is based on the Signal Space Separation (SSS) method 12a which has been discussed in patent application US 2006/0031038 (Simola et al.: "Method and System for processing a multi-channel measurement of magnetic fields") in detail. The core of the SSS method is that there are three volumes (or spaces) to be examined. The first volume includes all the interesting sources which are to be measured, that is, the human brain in this context. The second volume includes the measurement sensors so that this volume surrounds the first volume and is in rather close proximity to the first volume. The third volume includes all the interference sources around the aforementioned two volumes and thus, it can be infinite. Therefore, the third volume is a source area for all non-interesting and rather disturbing electromagnetic sources, whose effect should be cancelled in some manner. The SSS method is based on Maxwell's equations representing the theory of electromagnetism. The signal which is received in the second volume, can be divided into components which are represented as two different series developments. The convergence areas of the series developments can be examined. The main result of the SSS method is that the first source which is located in the first volume only affects the components of the first series development while the source in the third volume affects only the components of the second series development. In this manner, the magnetic sources clearly outside the measurement area (the sensor area) and the biomagnetic sources in the patient's head can be distinguished by examining the series developments.

Further as an application of the SSS method, the movement of the patient's head can be taken into account by attaching the channels to the coordinate system of the head.

Secondly, a concept of lead fields 12b is taken into use. Lead fields can be defined as a group of sensitivity vectors of a certain sensor. Concerning the primary current distribution in the source space, the lead field is a projection of the primary current vector to the specific direction of sensitivity in the current space as being also dependent on the measuring device, that is, the sensor and its sensitivity to the measurable magnetic fields.

With the SSS method, we can represent the signals from the physical channels as magnetostatic multipole moments 13a. By referring to 'Taulu, Kajola: "Presentation of electromagnetic multichannel data: The signal space separation method"', the multipole moments x can be achieved from the equation:

$$\Phi = Sx = [\,S_{in}\ \ S_{out}\,] \cdot \begin{bmatrix} x_{in} \\ x_{out} \end{bmatrix} \quad (2)$$

where φ is the measured signal vector, S is the SSS basis vector (the magnetic subspace) and x is the multipole moment vector. Notations "in" and "out" refer to the biomagnetic sources and the external interferences, respectively.

One core idea in the present invention is that by combining the use of the SSS method and the concept of lead fields, the achieved lead fields are orthogonal. Because of the orthogonality, the multipole moments represent a compact form for the measured information conveyed by the physical sensors. When the multipole moments are presented with such simple and mutually non-correlating basis vectors as a linearly converted expansion, the further analysis is simpler.

Another core issue in this point is that by estimating the multipole moments 13a the user achieves a set of virtual channels 13b which are point-like virtual sensors. The method according to the invention can be regarded as a spatial method for processing measured biomagnetic data. This means that the data which represented the geometry of the measurement setup at the beginning, is effectively removed 14 from the virtual channels. The geometry includes the mutual distances and locations between the different objects relating to that specific measurement setup. However, all relevant data is maintained in the virtual channel information. Another main issue in this transformation of channel array data is that the number of virtual channels is in the preferred embodiment significantly lower than the number of physical channels. In one embodiment, the number of virtual channels is one-fourth of the number of physical sensors used.

With less channels to be processed, the source modelling procedure is made less complex. It is possible to find a stable solution for the source locations and source activity with less assumptions or restricting estimates having to be made beforehand.

In other words, the SSS method decomposes time-dependent measurement signals into harmonic time-dependent amplitudes of orthogonal basis functions. This can be formulated in terms of vector spherical harmonic (VSH) functions which lead to a compact orthogonal lead field basis. Thus, the SSS decomposes M measured signals into N independent VSH channels where N<<M. Furthermore, the noises in each physical sensor are also converted into the noises in the VSH amplitudes.

An analogy for the aforementioned transform 13a, 13b can be seen in the concept of transfer function in the theory of electrical engineering. The lead fields can be thought as a transfer function between the current distribution in the conductive source volume (which is the human brain in this context) and the virtual channels to be determined. When lead fields are known with the help of the SSS method, the virtual channels with lesser amount of channels can be determined without any loss of relevant and useful information.

Another analogy for the aforementioned transform 13a, 13b is the use of the Fourier transform. In that analogy the physical channels represent the signal in the time domain and the virtual channels represent the signal in the frequency domain. No data is lost but the information is transferred to a form which is more illustrative and efficient to be processed further.

Shannon's concept of total information 15a can now be effectively introduced to the method according to the invention. According to the Shannon theorem:

$$I_{tot} = \frac{1}{2}\sum_{i=1}^{N} \log_2(SNR_i + 1), \quad (3)$$

where $SNR_i$ is the power signal to noise ratio of the i:th channel and N is the number of calculated channels, the total information $I_{tot}$ can be calculated in any signal presentation, where the channels and their noises are uncorrelated with each other. Because the virtual channels are orthogonal with each other, they are uncorrelated, that is, each virtual channel is independent of the other virtual channels. Also, the noises can be made uncorrelated by an operation which is effectively a rotation of a linear basis. The operation is taken into account both in the virtual channels and in the noise values. Thus, the Shannon's theorem (3) can be applied directly. The unit of the total information ($I_{tot}$) is bits per sample. It would not be reasonable to apply equation (3) directly to the physical sensor measurement data because there always exists significant redundancy in such MEG measurement signals.

The total information is therefore extracted 15b from the array of virtual channels according to equation (3). This characteristic is illustrative in many ways. For example, it can be used as a robust quantity measuring the physiological state of the patient 16a. Furthermore, the total information can be used for identifying virtual channels which are not including any useful information 16b. This can be performed by choosing different combinations of virtual channels, calculating total information for each combination and seeing whether the abandonment of certain virtual channels doesn't affect the total information parameter. Such channels can be cancelled from further processing and thus, making the post-processing even simpler.

A third application of the total information calculation is the optimization of the SSS algorithm 16c, that is, the decomposition results themselves. When the total information is at its maximum, the noise is at its minimum. Even in the case where external interferences have been identified and cancelled with the help of two multipole expansions of SSS, the maximum total information indicates the most accurately processed MEG measurement data for source modelling and other post-processing procedure for making e.g. a diagnosis of a cerebral disease.

Within the scope of the invention, the total information parameter can be used in any other purpose which is noted to be useful.

Figure 2:
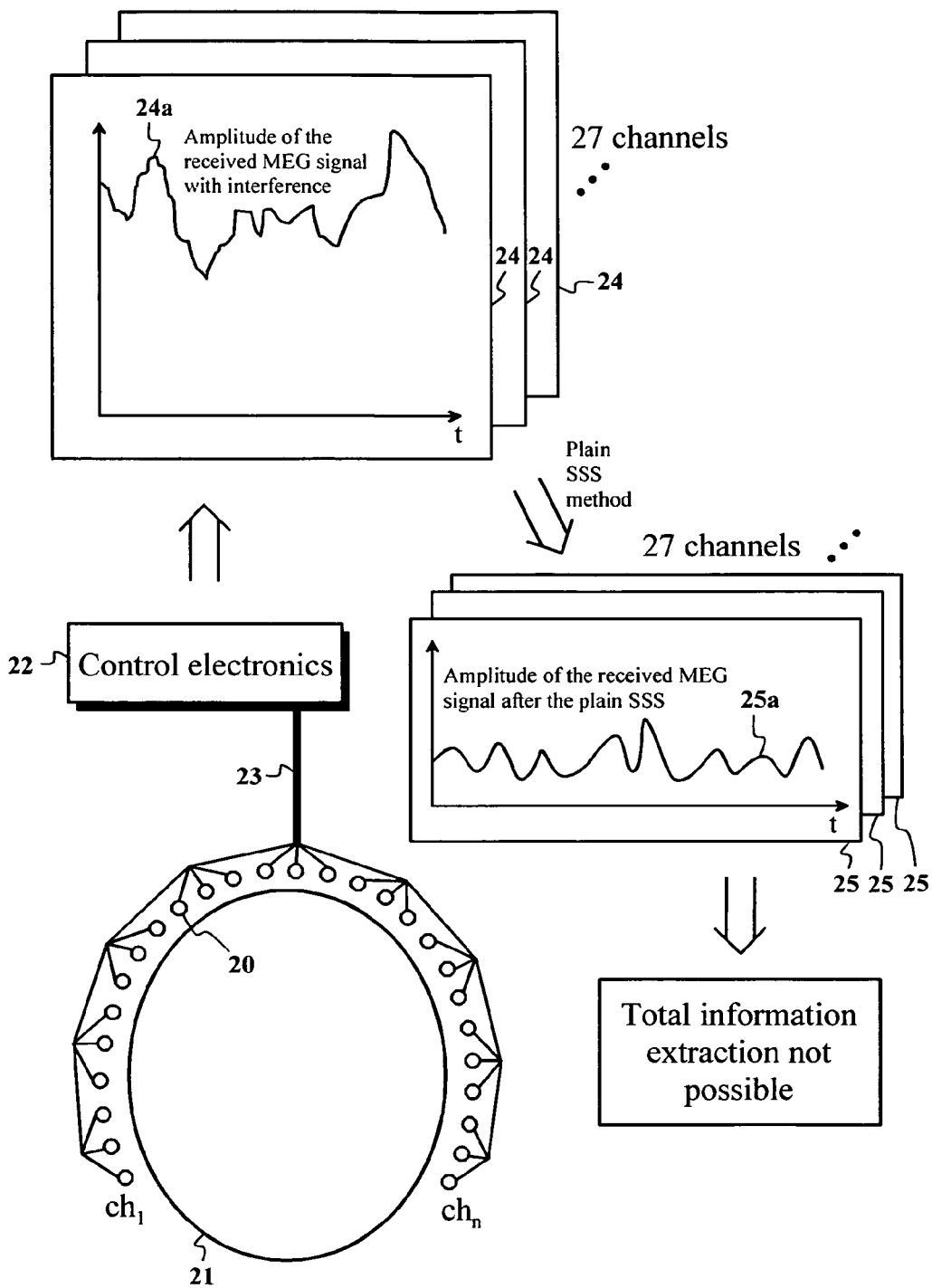
FIG. 2 is an illustration showing the apparatus with physical sensors as a starting point for the present invention and illustrations of the method according to prior art.
Figure 3:
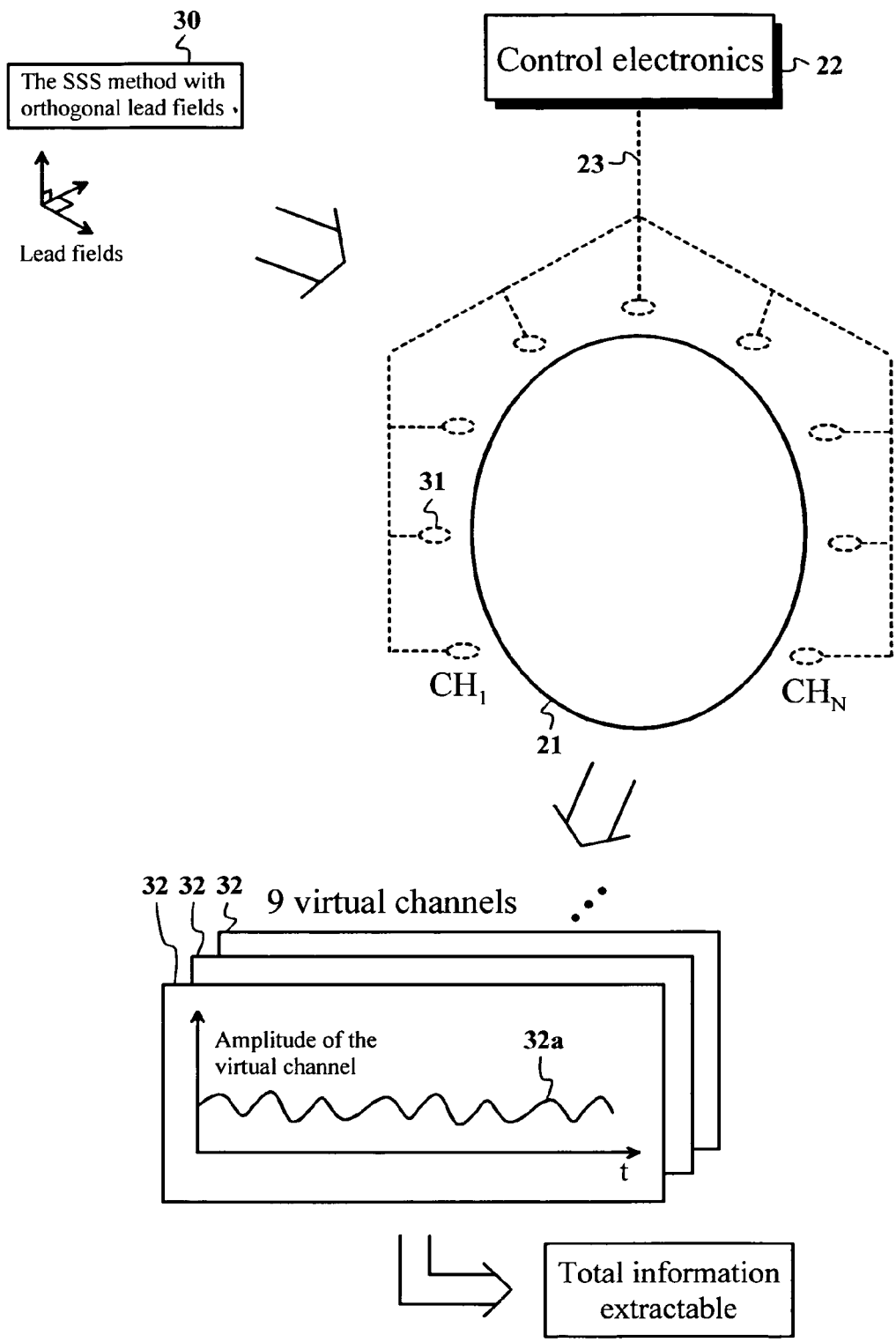
FIG. 3 is an illustration showing the transformation into virtual channels according to an embodiment of the present invention.

Referring now to FIGS. 2 and 3, a simplified picture of the needed apparatus is shown. FIG. 2 shows an embodiment of the physical setup of the apparatus for both the methods according to prior art and the present invention. However, FIG. 2 illustrates additionally some method steps according to prior art while FIG. 3 illustrates the idea of the present invention. In FIG. 2, patient's head 21 is surrounded by physical sensors 20 such as SQUIDs. In practise in EEG measurements, these sensors 20 may be attached on the surface of the scalp. In MEG devices, the sensors 20 are located so that they are integrally part of the MEG measurement device situated near the patient's head 21. In this particular simplified example, there are twentyseven physical sensors or channels ch₁, ... chₙ. The amount of used sensors can naturally be different. For a typical MEG equipment this amount is 306 sensors.

The sensors 20 are connected 23 to the control electronics 22 which takes care of further processing of the received biomagnetic signals. The apparatus may be located in an interference shielded room or the device could include e.g. compensation actuators for diminishing the effect of external magnetic disturbances.

In FIG. 2, the curve 24a shows an illustration of the measured amplitude in one channel. The control electronics 22 receives twentyseven different curves 24 describing all measured data from channels chₙ.

In FIG. 2, plain SSS method is applied for cancelling external interferences. The result of this procedure is that we achieve the same amount of channels 25 which each depict the interesting biomagnetic signal (the amplitude) without interference 25a. In such an array of signals, the lead fields are not orthogonal and the total information can't be reliably extracted from such a representation of signals.

By using FIG. 2 as a starting point, the present invention has the same physical sensors 20. The control electronics 22 achieves similarly the array of signals 24 which include the external interferences. However, as described earlier as a characterising step according to the invention, the SSS method is introduced with orthogonal lead fields 30 so that multipole moments are calculated with harmonic functions as was described with the steps 13a and 13b of FIG. 1. As a result, the situation from the point of view of the measuring sensors is that the physical sensors ch₁ ... ch₂₇ 20 are replaced by an array of virtual sensors CH₁ ... CH₉ 31 which function the same way as real sensors. The data captured by the virtual sensors 31 is the same with the exception that the data including the geometry of that specific measurement is effectively removed.

As a result, the control electronics 22 achieves nine virtual signal channels 32 whose amplitudes are represented as curves 32a. All the relevant information originated from the sources in the volume 21, which was present in channels 25, is also present in channels 32, though the number of needed channels 32 is a fraction of those in FIG. 2. In this simplified example this fraction is ⅓ but in a typical arrangement this fraction is 80/306≈26%.

In the representation of channels 32, the lead fields are orthogonal, which means that the total information parameter can be extracted directly. This parameter can further be used in various ways, as was earlier described in context with FIG. 1.

The present invention can be applied for either EEG or MEG measurements.

The invention can be implemented by using a computer program where the code performs the method steps disclosed earlier.

It is obvious to a person skilled in the art that with the advancement of technology, the basic idea of the invention may be implemented in various ways. The invention and its embodiments are thus not limited to the examples described above, instead they may vary within the scope of the claims.

The invention claimed is:

1. A method for spatial processing of multi-channel measurement data implemented on a control electronics, comprising:
    measuring multi-channel data with plurality of sensors;
    estimating by the control electronics from the measured data, by using a Signal Space Separation method, signals representing biomagnetic sources and signals representing sources outside of a sensor area; and presenting, by the control electronics, the estimated signals as multipole moments having orthogonal lead field expressions, resulting in virtual channel data with dissipated measurement geometry data and with less channels than the number of the plurality of sensors.

2. The method according to claim 1, wherein in the estimation step is performed with a signal space separation Signal Space Separation method, a magnetic field that was registered using a multi-channel measuring device, is analysed in a geometry in which the sources of interest are disposed in volume V1; the sensors measuring the field or the components thereof in volume V2 outside volume V1; and sources of magnetic interference and compensating actuators in volume V3 outside both volumes V1 and V2, wherein volume V3 can be infinite, wherein the Signal Space Separation method further comprises the steps of:
    parametrising in volume V2 the magnetic field produced by the sources of interest as a sum of elementary fields, each of them being irrotational, sourceless and finite outside volume V1 so that a presentation of a desired accuracy is achieved for the parametrised magnetic field in volume V2;
    parametrising in volume V2 the sum magnetic field produced by the interference sources and the compensating actuators as a sum of elementary fields, each of them being irrotational, sourceless and finite outside volume V3 so that a presentation of a desired accuracy is achieved for the parametrised magnetic field in volume V2;
    calculating the signal vector of the measuring device corresponding to each elementary field;
    measuring the magnetic signal using sensors; and
    separating the fields produced by sources disposed in different volumes by estimating the components of the measured signal vector in the basis formed by the signal vectors associated with the elementary fields.

3. The method according to claim 2, the method further comprising:
    identifying and processing external interferences with the signal space separation Signal Space Separation method; and
    cancelling the external interferences from the measurement data.

4. The method according to claim 2, the method further comprising:
    identifying movement of a patient's head; and
    cancelling the effect of the movement of the patient's head with the Signal Space Separation method.

5. The method according to claim 1, the method further comprising:
    estimating the multipole moments with vector spherical harmonic functions.

6. The method according to claim 1, the method further comprising:
    extracting total information from the data represented in virtual channels.

7. The method according to claim 6, the method further comprising:
    calculating the total information $I_{tot}$ with a formula $$I_{tot} = \frac{1}{2}\sum_{i=1}^{N} \log_2(SNR_i + 1).$$

where $SNR_i$ is the power signal to noise ratio of the i:th channel and N is the number of calculated channels.

8. The method according to claim 6, the method further comprising:
using the total information for estimating the physiological state of the patient, or for identifying and abandoning non-useful virtual channels or for optimizing the Signal Space Separation decomposition results.

9. The method according to claim 1, the method further comprising:
setting the virtual channels represented by the multipole moments as point-like.

10. The method according to claim 1, wherein the method is applied in a magnetoencephalographic measurement.

11. The method according to claim 1, wherein the method is applied in an electroencephalographic measurement.

12. A multi-channel measuring device for spatial processing of multi-channel measurement data, comprising:
a sensor array comprising plurality of sensors for measuring multi-channel data; and
a control electronics configured to estimate from the measured data, by using a Signal Space Separation method, signals representing biomagnetic sources and signals representing sources outside of a sensor area;
the control electronics configured to present the estimated signals as multipole moments having orthogonal lead field expressions, resulting in virtual channel data with dissipated measurement geometry data and with less channels than the number of the plurality of sensors.

13. The device according to claim 12, wherein the control electronics is configured to perform the Signal Space Separation method, wherein a magnetic field that was registered using the multi-channel measuring device, is analysed in a geometry in which the sources of interest are disposed in volume V1; the sensors measuring the field or the components thereof in volume V2 outside volume V1; and sources of magnetic interference and compensating actuators in volume V3 outside both volumes V1 and V2, wherein volume V3 can be infinite, wherein the control electronics is further configured to perform the steps of:
parametrising in volume V2 the magnetic field produced by the sources of interest as a sum of elementary fields, each of them being irrotational, sourceless and finite outside volume V1 so that a presentation of a desired accuracy is achieved for the parametrised magnetic field in volume V2;
parametrising in volume V2 the sum magnetic field produced by the interference sources and the compensating actuators as a sum of elementary fields, each of them being irrotational, sourceless and finite outside volume V3 so that a presentation of a desired accuracy is achieved for the parametrised magnetic field in volume V2;
calculating the signal vector of the measuring device corresponding to each elementary field;
measuring the magnetic signal using sensors; and
separating the fields produced by sources disposed in different volumes by estimating the components of the measured signal vector in the basis formed by the signal vectors associated with the elementary fields.

14. The device according to claim 13, the device further comprising:
the control electronics configured to identify and process external interferences with the Signal Space Separation method; and
compensating actuators and the control electronics configured to cancel the external interferences from the measurement data.

15. The device according to claim 13, the device further comprising:
the control electronics configured to identify movement of the patient's head; and
the control electronics configured to cancel the effect of the movement of the patient's head with the Signal Space Separation method.

16. The device according to claim 12, the device further comprising:
the control electronics configured to estimate the multipole moments with vector spherical harmonic functions.

17. The device according to claim 13, the device further comprising:
the control electronics configured to extract total information from the data represented in virtual channels.

18. The device according to claim 17, the device further comprising:
the control electronics configured to calculate the total information $I_{tot}$ with a formula $$I_{tot} = \frac{1}{2}\sum_{i=1}^{N} \log_2(SNR_i + 1),$$

where $SNR_i$ is the power signal to noise ratio of the i:th channel and N is the number of calculated channels.

19. The device according to claim 17, the device further comprising:
the control electronics configured to use the total information for estimating the physiological state of the patient, or for identifying and abandoning non-useful virtual channels or for optimizing the Signal Space Separation decomposition results.

20. The device according to claim 12, the device further comprising:
the control electronics configured to set the virtual channels represented by the multipole moments as point-like.

21. The device according to claim 12, wherein the device is a MEG measuring device.

22. The device according to claim 12, wherein the device is an EEG measuring device.

23. A computer program implemented on a non-transitory computer readable medium for spatial processing of multi-channel measurement data by a control electronics, comprising code adapted to perform the following steps when executed on a data-processing system:
measuring multi-channel data with plurality of sensors; and
estimating by the control electronics from the measured data, by using a Signal Space Separation method, signals representing biomagnetic sources and signals representing sources outside of a sensor area; and
presenting, by the control electronics, the estimated signals as multipole moments having orthogonal lead field expressions, resulting in virtual channel data with dissipated measurement geometry data and with less channels than the number of the plurality of sensors.

24. The computer program according to claim 23, further adapted to perform the estimating step with wherein in the Signal Space Separation method, a magnetic field that was registered using a multi-channel measuring device, is analysed in a geometry in which the sources of interest are disposed in volume V1; the sensors measuring the field or the components thereof in volume V2 outside volume V1; and sources of magnetic interference and compensating actuators in volume V3 outside both volumes V1 and V2, wherein volume V3 can be infinite, wherein the Signal Space Separation_method further comprises the steps of:

parametrising in volume V2 the magnetic field produced by the sources of interest as a sum of elementary fields, each of them being irrotational, sourceless and finite outside volume V1 so that a presentation of a desired accuracy is achieved for the parametrised magnetic field in volume V2;

parametrising in volume V2 the sum magnetic field produced by the interference sources and the compensating actuators as a sum of elementary fields, each of them being irrotational, sourceless and finite outside volume V3 so that a presentation of a desired accuracy is achieved for the parametrised magnetic field in volume V2;

calculating the signal vector of the measuring device corresponding to each elementary field;

measuring the magnetic signal using sensors; and separating the fields produced by sources disposed in different volumes by estimating the components of the measured signal vector in the basis formed by the signal vectors associated with the elementary fields.

25. The computer program according to claim 24, further adapted to perform the steps of:
identifying and processing external interferences with the Signal Space Separation method; and
cancelling the external interferences from the measurement data.

26. The computer program according to claim 24, further adapted to perform the steps of:
identifying movement of the patient's head with the Signal Space Separation method; and
cancelling the effect of the movement of the patient's head.

27. The computer program according to claim 23, further adapted to perform the step of:
estimating the multipole moments with vector spherical harmonic functions.

28. The computer program according to claim 23, further adapted to perform the step of:
extracting total information from the data represented in virtual channels.

29. The computer program according to claim 28, further adapted to perform the step of:
calculating the total information $I_{tot}$ with a formula $$I_{tot} = \frac{1}{2}\sum_{i=1}^{N} \log_2(SNR_i + 1),$$

where $SNR_i$ is the power signal to noise ratio of the i:th channel and N is the number of calculated channels.

30. The computer program according to claim 28, further adapted to perform the step of:
using the total information for estimating the physiological state of the patient, or for identifying and abandoning non-useful virtual channels or for optimizing the Signal Space Separation_decomposition results.

31. The computer program according to claim 23, further adapted to perform the step of:
setting the virtual channels represented by the multipole moments as point-like.

32. The computer program according to claim 23, wherein the computer program is applied in a magnetoencephalographic measurement.

33. The computer program according to claim 23, wherein the computer program is applied in an electroencephalographic measurement.

* * * * *